United States Patent [19]

Abramowitz

[11] Patent Number: 4,950,233
[45] Date of Patent: Aug. 21, 1990

[54] NERVE BLOCK NEEDLE AND SAFETY METHOD OF USE

[76] Inventor: Joseph M. Abramowitz, 18 Covert St., Port Washington, N.Y. 11050

[21] Appl. No.: 253,777

[22] Filed: Oct. 5, 1988

[51] Int. Cl.$^5$ ............................................. A61M 31/00
[52] U.S. Cl. ...................................... 604/51; 604/272
[58] Field of Search .................................. 604/48–51, 604/117, 239, 264, 272, 93, 181, 188

[56] References Cited

U.S. PATENT DOCUMENTS

| | | | |
|---|---|---|---|
| 1,125,887 | 1/1915 | Schimmel | 604/239 |
| 3,854,477 | 12/1974 | Smith | 604/51 |
| 4,186,750 | 2/1980 | Patel | 604/272 |
| 4,215,699 | 8/1980 | Patel | 604/272 |
| 4,518,383 | 5/1985 | Evans | 604/272 |
| 4,586,921 | 5/1986 | Berson | 604/49 |
| 4,747,824 | 5/1988 | Spinello | 604/51 |
| 4,759,746 | 7/1988 | Straus | 604/272 |

Primary Examiner—John D. Yasko
Assistant Examiner—Anthony M. Gutowski
Attorney, Agent, or Firm—Albert M. Zalkind

[57] ABSTRACT

A nerve block needle is curved in a manner for use in penetrating skin and muscle at the side of a rib, so as to have the tip re-entrant, in the direction of and proximate to the groove in the inner surface of the rib, the said groove carrying the intercostal vein artery and nerve. A conventional local anesthetic drug can then be introduced in close proximity to the intercostal nerve with enhanced safety with respect to puncturing and collapse of the underlying lung. Such complication, known as pneumothorax, may occur with the use of a conventional straight nerve block needle. Other advantages of the curved needle and method of use will be subsequently explained.

2 Claims, 1 Drawing Sheet

NERVE BLOCK NEEDLE AND SAFETY METHOD OF USE

BACKGROUND OF THE INVENTION

Conventional nerve block needles are hollow straight needles for conducting local anesthetic solution into close proximity of the nerve to be blocked, i.e., anesthetized. Most peripheral nerves in the body are easily blocked with a straight needle because they are easily accessible, being unobscured by bony structures. The intercostal nerves are exceptions as they are inaccessible, being situated in a groove in the inside arcuate surface of the ribs, one nerve per rib. Furthermore lung tissue is situated millimeters away from the nerves at a deeper level. It is difficult to get close to the nerve to be blocked with a straight needle since it must clear the rib to get to the nerve area and injection then has to be made at a distance from the nerve. This risks failure of the block unless a large volume of anesthetic solution is used. Large volumes are dangerous if multiple nerves are to be blocked, as this risks a systemic toxic reaction from overdosage which may be fatal.

Additionally, lung tissue being situated millimeters away from the intercostal nerves, needle puncture of the lung causes air to leak outside the lung with subsequent collapse of the lung, the complication known as a pneumothorax. It is a potentially fatal condition if not recognized and appropriately treated. Diagnosis and treatment involves complexity and expense including diagnostic and subsequent chest X-rays, treatment procedures, prolonged hospitalization, and additional work for health care personnel.

It will thus be evident from the foregoing that the technique of intercostal nerve block requires much precision and skill. A method which increases the ease of performance and minimizes the risk has obvious advantages.

A known prior art method consists of pushing a straight needle through the skin directly onto the surface of the rib and then "walking" the needle off the lower edge of the rib in a number of short steps critically feeling for the step where the needle slips off the lower edge of the rib. When this critical event occurs, the needle is positioned underneath the rib, the depth of penetration being then determined by the skill and judgment of the operator. With the needle tip in ultimate position, injection of drug, i.e., local anesthetic into the nerve area by conventional syringe is performed. Whilst the complication of pneumothorax is admittedly rare, near misses are far more common. In an era of malpractice allegations and cost containment in medicine a potential for diminution or abolition of risk is obviously advantageous and not to be disregarded.

BRIEF DESCRIPTION OF THE PRESENT INVENTION

The present invention uses a hollow needle, suitably curved, which, due to its design and differing method of use, minimizes the shortcomings of the prior art straight needles. The point can be guided to traverse a path somewhat around a center of curvature, such that it pierces skin and muscle and comes re-entrantly to the vicinity of the nerve by a circuitous route rather than a linear one. This circuitous route ensures that when the needle tip is closest to the lung, it is not moving towards the lung, but initially parallel to the lung surface and then away from it.

A detailed description of the invention now follows, in which.

Figure 1:
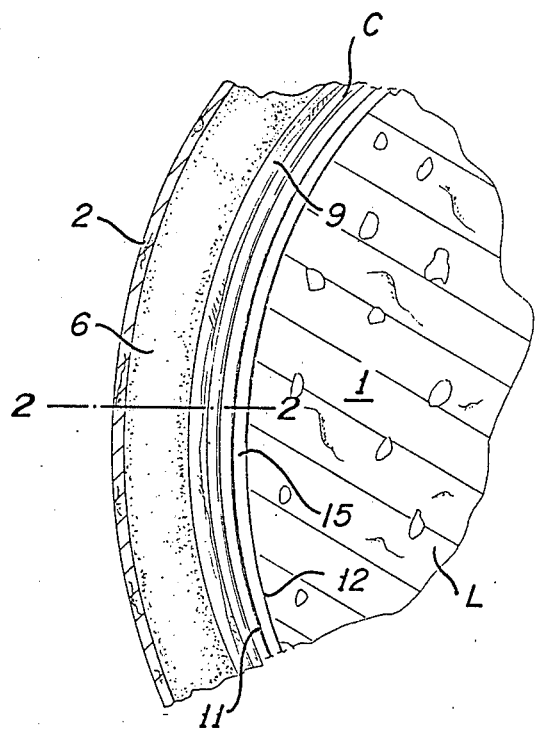
FIG. 1 is a fragmentary vertical section through a rib of a patient on his back.

Referring to FIG. 1, the vertical section of the rib 6 has a channel C, which houses an intercostal nerve 9. Lining inside the chest wall, parietal pleura 11, is shown, together with lining outside of the lung tissue L, visceral pleura 12.

A so-called pleura space 15 is shown, which is a potential space between the two previously named pleural linings, 11 and 12.

Figure 2:
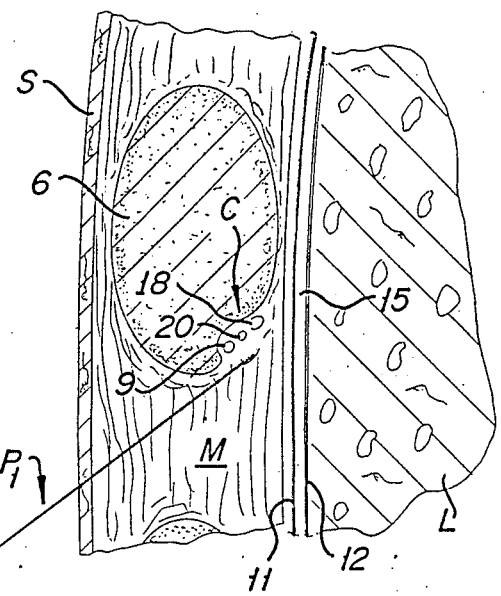
FIG. 2 is a magnified transverse section on the line 2—2 of FIG. 1 showing the use of a juxtaposed prior art straight needle in relation to the area or region of the intercostal nerve, and the lung tissue.

Referring now to FIG. 2, a transverse section through the rib on the section line 2—2 of FIG. 1 shown, indicating the channel C in the lower inner corner of the rib in which is housed the intercostal vein 18, the intercostal artery 20, and the intercostal nerve 9.

Likewise are shown the lining 11 inside of the chest wall, and the lining 12 outside of the lung, and the pleura space 15 between the linings.

Represented is the skin S and a muscle layer M. It will be noted that a prior art straight needle 22 at point of entry $P_1$ passes through the skin and muscle to ultimately come perilously close to the pleura layers exterior of the lung, and with too much forward motion could pierce the lung. Also, note that the angle of the needle would necessarily direct the drug away from the intercostal nerve 9, rather than toward it, as compared with a curved needle and method of the invention, FIG. 3.

Figure 3:
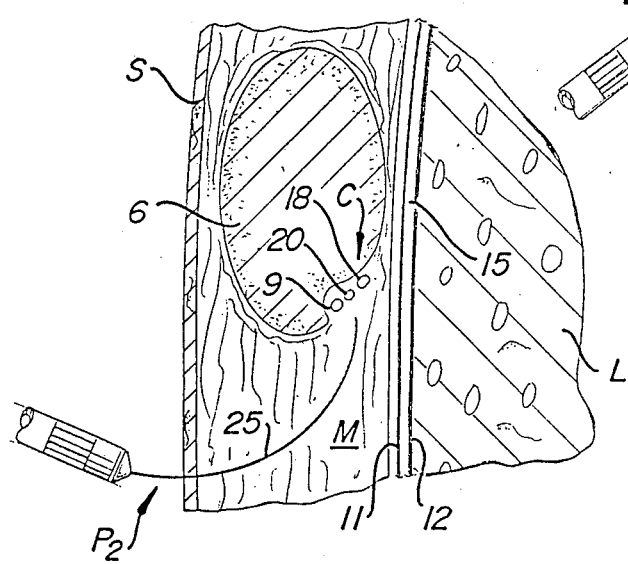
FIG. 3 is a view similar to FIG. 2 showing the use of a juxtaposed curved needle.

Referring now to FIG. 3, a curved needle 25 is shown with a point of entry $P_2$ through the skin.

The manner in which the needle is used first requires location of a point of entry $P_2$ on the skin. A point is chosen on the skin so that the tip pierces the skin and is advanced to contact the rib surface. The needle is then "walked off" the rib, moving towards the lower border of the rib. Once the needle tip clears the lower rib border, it is rotated following its curvature. Due to the curvature of the needle it will follow an arcuate track, with the tip ultimately re-entrant, i.e., arching toward the rib and away from the lung area. When, in the judgment of the anesthesiologist, penetration is sufficient and the needle tip is an close as possible to the intercostal nerve, the blocking agent is then forced into the area from a syringe.

It will be appreciated by comparison of FIGS. 2 and 3 that in it's re-entrant position, the curved needle tip is directed toward the nerve. In the case of the prior art straight needle, the tip is directed away from the nerve. Thus, the volume of local anesthetic solution required to produce an effective nerve block is less and the greater the chance of a successful block. These are added advantages of the invention.

It will be appreciated that needles of varying size are contemplated to meet varying circumstances such as body size and shape.

In retrospect, the path of the straight needle tends to bypass the nerve rather than approach it, as compared with the curved needle and method of the invention.

The invention brings the blocking agent as close as possible to the intercostal nerve, whereas with the prior art the straight needle type tip tends to bypass the nerve.

I claim:

1. A safety method of administering a nerve block drug to an intercostal nerve in the channel of a rib which method comprises penetrating the body of a patient with an arcuate needle at an angle to the rib; pressing the needle so as to have it follow its own curvature in the body until the needle tip is re-entrant in a direction generally toward the nerve and away from the lung and within the area where a drug injected through the needle can reach the nerve; and injecting a nerve block drug through the needle.

2. A safety method of administering a nerve block drug to an intercostal nerve in the channel of a rib to avoid lung puncture which method comprises locating the point of entry in a patient's skin and penetrating the body of the patent with the tip of an acurate needle at an angle to the rib; advancing the needle tip to contact the rib surface; walking the needle tip off the lower border of the rib; rotating the needle to follow its own curvature in the body until the needle tip is re-entrant in a direction generally toward the nerve and away from the lung and within the area where a drug injected through the needle can reach the nerve; and injecting a nerve block drug through the needle.

* * * * *

UNITED STATES PATENT AND TRADEMARK OFFICE
CERTIFICATE OF CORRECTION

PATENT NO. : 4,950,233

DATED : Aug. 21, 1990

INVENTOR(S) : Joseph M. Abramowitz

It is certified that error appears in the above-identified patent and that said Letters Patent is hereby corrected as shown below:

COLUMN 4;
Claim 2, line 5, the word "acurate" should be arcuate.

Signed and Sealed this

Twenty-ninth Day of September, 1992

Attest:

DOUGLAS B. COMER

Attesting Officer      Acting Commissioner of Patents and Trademarks